(12) United States Patent
Cho et al.

(10) Patent No.: US 10,106,694 B2
(45) Date of Patent: Oct. 23, 2018

(54) STRUCTURE FOR OPTICAL ANALYSIS AND INK COMPOSITION FOR MANUFACTURING THE SAME

(71) Applicant: SAMSUNG ELECTRONICS CO., LTD., Suwon-si (KR)

(72) Inventors: Euy Hyun Cho, Suwon-si (KR); Ji Yun Kang, Suwon-si (KR); Ji Won Kim, Suwon-si (KR); Sung Ha Park, Suwon-si (KR); Beom Seok Lee, Osan-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 215 days.

(21) Appl. No.: 14/753,378

(22) Filed: Jun. 29, 2015

(65) Prior Publication Data
US 2016/0168398 A1 Jun. 16, 2016

(30) Foreign Application Priority Data
Dec. 16, 2014 (KR) .................. 10-2014-0181276

(51) Int. Cl.
*G01N 1/10* (2006.01)
*C09D 11/03* (2014.01)
(Continued)

(52) U.S. Cl.
CPC ............ *C09D 11/03* (2013.01); *B01L 3/5027* (2013.01); *B01L 3/502707* (2013.01);
(Continued)

(58) Field of Classification Search
None
See application file for complete search history.

(56) References Cited

U.S. PATENT DOCUMENTS 4,725,388 A * 2/1988 Nelson .................. B01L 3/5085
264/21
5,350,676 A 9/1994 Oberhardt et al.
(Continued)

FOREIGN PATENT DOCUMENTS

JP 2008-180764 A 8/2008
WO 2011/157895 A1 12/2011

OTHER PUBLICATIONS

International Search Report for PCT/KR2015/007208 dated Oct. 22, 2015 [PCT/ISA/210].
(Continued)

*Primary Examiner* — Tri Ton
*Assistant Examiner* — Rufus Phillips
(74) *Attorney, Agent, or Firm* — Sughrue Mion, PLLC

(57) ABSTRACT

Disclosed herein are a structure for optical analysis that is capable of optically analyzing a small amount of a sample and an ink composition for manufacturing the same. A structure for optical analysis includes a support and an ink structure coupled to the support and configured to form a chamber on one surface of the support. The ink structure includes a first ink structural component configured to form a body of the ink structure and a second ink structural component formed at a lower portion of a side surface of the first ink, such that the first ink structural component and the second ink structural component have different slopes with respect to a direction of a center of the chamber.

18 Claims, 30 Drawing Sheets

(51) Int. Cl.
  *G01N 21/03*   (2006.01)
  *C09D 11/037*  (2014.01)
  *B01L 3/00*    (2006.01)
  *G01N 33/53*   (2006.01)
  *G01N 21/77*   (2006.01)

(52) U.S. Cl.
  CPC ........... *C09D 11/037* (2013.01); *G01N 21/03* (2013.01); *G01N 21/77* (2013.01); *G01N 33/53* (2013.01); *B01L 2300/0816* (2013.01); *B01L 2300/0887* (2013.01); *B01L 2300/161* (2013.01); *G01N 2021/0325* (2013.01); *G01N 2021/0346* (2013.01)

(56) References Cited

U.S. PATENT DOCUMENTS

| | | | |
|---|---|---|---|
| 5,581,086 A * | 12/1996 | Ben-Menachem | ............................ G01N 21/3577 250/338.1 |
| 5,585,275 A * | 12/1996 | Hudson | ................ B01D 61/18 422/129 |
| 5,842,106 A * | 11/1998 | Thaler | ................ B01F 13/0077 419/10 |
| 6,077,660 A | 6/2000 | Wong et al. | |
| 6,705,357 B2 * | 3/2004 | Jeon | ................ B01F 5/0601 141/100 |
| 2001/0021726 A1 | 9/2001 | Brown | |
| 2001/0036674 A1 | 11/2001 | Indermuhle et al. | |
| 2002/0150506 A1 * | 10/2002 | Okamoto | ............. B01J 19/0046 422/68.1 |
| 2002/0155035 A1 * | 10/2002 | Kansy | ................ B01L 3/50255 422/547 |
| 2004/0067166 A1 | 4/2004 | Karinka et al. | |
| 2005/0048575 A1 * | 3/2005 | Coassin | ............. B01L 3/50851 435/7.1 |
| 2006/0254916 A1 | 11/2006 | Hernandez et al. | |
| 2008/0019871 A1 * | 1/2008 | Sakamoto | ............... B01L 3/545 422/68.1 |
| 2008/0160539 A1 | 7/2008 | Murphy et al. | |
| 2009/0060791 A1 | 3/2009 | Hagiwara et al. | |
| 2009/0253857 A1 | 10/2009 | Parris et al. | |
| 2010/0159146 A1 * | 6/2010 | Chilla | ...................... B05D 7/14 427/407.1 |
| 2010/0326844 A1 * | 12/2010 | Hyland | ............... B81C 1/00119 205/777.5 |
| 2011/0174618 A1 | 7/2011 | Bryan | |
| 2012/0242748 A1 | 9/2012 | Katakis et al. | |
| 2015/0005174 A1 * | 1/2015 | Tanaka | .................... B32B 27/36 504/360 |
| 2015/0184119 A1 * | 7/2015 | Tsukada | ................. C12M 23/12 506/10 |

OTHER PUBLICATIONS

Communication dated Nov. 30, 2017, issued by the European Patent Office in counterpart European Patent Application No. 15870147.4.

* cited by examiner

STRUCTURE FOR OPTICAL ANALYSIS AND INK COMPOSITION FOR MANUFACTURING THE SAME

CROSS-REFERENCE TO RELATED APPLICATION

This application claims priority from Korean Patent Application No. 10-2014-00181276, filed on Dec. 16, 2014 in the Korean Intellectual Property Office, the disclosure of which is incorporated herein by reference in its entirety.

BACKGROUND

1. Field

Exemplary embodiments relate to a structure for optical analysis that is capable of optically analyzing a small amount of sample and an ink composition for manufacturing the structure for optical analysis.

2. Description of the Related Art

The samples of patients may be analyzed by using optical analysis for immunoassays, clinical laboratory tests and the like. These immunoassays and clinical laboratory tests are important for the diagnosis and treatment of patient states.

A structure for optical analysis may be provided for the optical analysis of the samples of patients, and the optical analysis structure may include a pigment structure coated with a pigment-based ink and a resin structure coated with a resin-based ink.

In the optical analysis structure, since the pigment structure has many holes on a surface thereof, a phenomenon in which a sample permeates a hole may occur, and since the resin structure has a small contact angle, a phenomenon in which a sample overflowing out of the structure may occur.

SUMMARY

One aspect of one or more exemplary embodiments provides a structure for optical analysis which includes a first ink structural component configured to form the body of an ink structure, and a second ink structural component formed at a lower portion of a side surface of the first ink structural component.

Another aspect of one or more exemplary embodiments provides a structure for optical analysis which includes an ink structure coated with an ink composition having a pigment-based ink and a resin-based ink.

Additional aspects of the exemplary embodiments will be set forth in part in the description which follows and, in part, will be apparent from the description, or may be learned by practice of the exemplary embodiments.

In accordance with one aspect, a structure for optical analysis includes a support and an ink structure coupled to the support and configured to form a chamber on one surface of the support, and the ink structure includes a first ink structural component configured to form a body of the ink structure and having a first slope with respect to a direction of a center of the chamber and a second ink structural component formed at a lower portion of a side surface of the first ink structural component and having a second slope with respect to the direction of a center of the chamber, wherein the first slope is different from the second slope.

The second ink structural component may have a higher lipophilicity than the first ink structural component.

A slope of a longitudinal section of the second ink structural component may decrease along a direction of the support.

A longitudinal section of the second ink structural component may have a parabolic shape or a Gaussian distribution shape.

A diameter of the chamber may decrease from a starting point of the second ink structural component in a direction of the support.

The ink structure may form a channel on one surface of the support.

A width of the channel may decrease from a starting point of the second ink structural component in a direction of the support.

The ink structure may be formed by coating an ink composition that includes a pigment-based ink and a resin-based ink.

The first ink structural component may be formed of the pigment-based ink and the resin-based ink.

The second ink structural component may be formed of the resin-based ink.

The second ink structural component may be formed by the resin-based ink in the ink composition flowing downward in a gravitational direction.

A weight of the pigment-based ink may comprise between 30% and 70% of a total weight of the ink composition, and a weight of the resin-based ink may comprise between 30% and 70% of the total weight of the ink composition.

The ink composition may further include a curing agent and a retardant such that a combined weight of the curing agent and the retardant comprises between 10% and 20% of a total weight of the ink composition.

A transmittance of the ink structure may increase in correspondence with an increase of an ink composition ratio of a white resin-based ink included in the ink composition.

A transmittance of the ink structure may increase in correspondence with an increase of a wavelength of light that is incident onto the ink structure.

The pigment-based ink may include at least one from among rutile, anatase, antimony oxide, zinc, calcium carbonate, silica, cadmium, chromium, cobalt, copper, iron oxide, lead, manganese, mercury, titanium, carbon, clay earth, ultramarine, alizarin, alizarin crimson, gamboge, cochineal red, rose madder, indigo, Indian yellow, tyrian purple, quinacridone, magenta, phthalo green phthalo blue pigment red 170, and diarylide yellow.

The resin-based ink may include at least one from among silicone, cryptal, a semiconductor, benzoin, petroleum, styrene, aniline, an amino group, amino alkyd, vinyl acetate, alkyd, epoxy, urea, a casting resin, toluene, plastic, polyimide, polyurethane, and amber.

The support may be provided in a thin film shape of a film type.

The support may be provided in a curved surface shape.

In the support, one surface coupled to the ink structure may be hydrophilic-processed.

In accordance with another aspect, an ink composition for manufacturing a structure for optical analysis includes a pigment-based ink that has a weight that comprises between 30% and 70% of a total weight of the ink composition, and a resin-based ink that has a weight that comprises between 30% and 70% of the total weight of the ink composition.

The ink composition may further include a curing agent and a retardant, wherein a combined weight of the curing agent and the retardant comprises between 10% and 20% of the total weight of the ink composition.

The pigment-based ink may include at least one from among rutile, anatase, antimony oxide, zinc, calcium carbonate, silica, cadmium, chromium, cobalt, copper, iron oxide, lead, manganese, mercury, titanium, carbon, clay earth, ultramarine, alizarin, alizarin crimson, gamboge, cochineal red, rose madder, indigo, indian yellow, tyrian purple, quinacridone, magenta, phthalo green phthalo blue pigment red 170, and diarylide yellow.

The resin-based ink may include at least one from among silicone, cryptal, a semiconductor, benzoin, petroleum, styrene, aniline, an amino group, amino alkyd, vinyl acetate, alkyd, epoxy, urea, a casting resin, toluene, plastic, polyimide, polyurethane, and amber.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
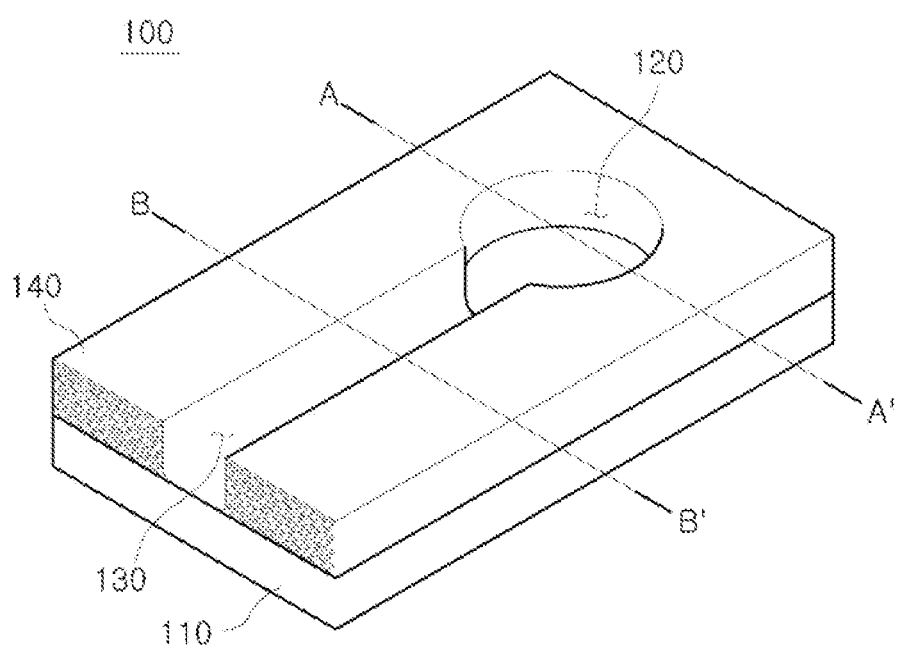
FIG. 1 is a perspective view illustrating an optical analysis structure, according to an exemplary embodiment.

Advantages and features of exemplary embodiments and methods of achieving the same will be clearly understood with reference to the accompanying drawings and the following detailed description of the exemplary embodiments. However, the present inventive concept is not limited to the exemplary embodiments to be disclosed, but may be implemented in various different forms. The exemplary embodiments are provided in order to fully explain the present inventive concept and fully explain the scope of the present inventive concept for those of skill in the art. The scope of the present inventive concept is defined by the appended claims. Hereinafter, the exemplary embodiments will be described in detail with reference to accompanying views.

Reference will now be made in detail to exemplary embodiments, examples of which are illustrated in the accompanying drawings, wherein like reference numerals refer to like elements throughout.

The exemplary embodiments relate to a structure for optical analysis and an ink composition configured to manufacture the same which is provided to conveniently control the movement of a sample that passes through the structure and to derive an optical analysis result having a uniform dispersion.

The optical analysis structure is applicable to all fields in which optical analysis is useful, because a sample is injected into the structure in optical analysis. Hereinafter, the optical analysis structure will be described in detail with accompanying views.

Figure 2:
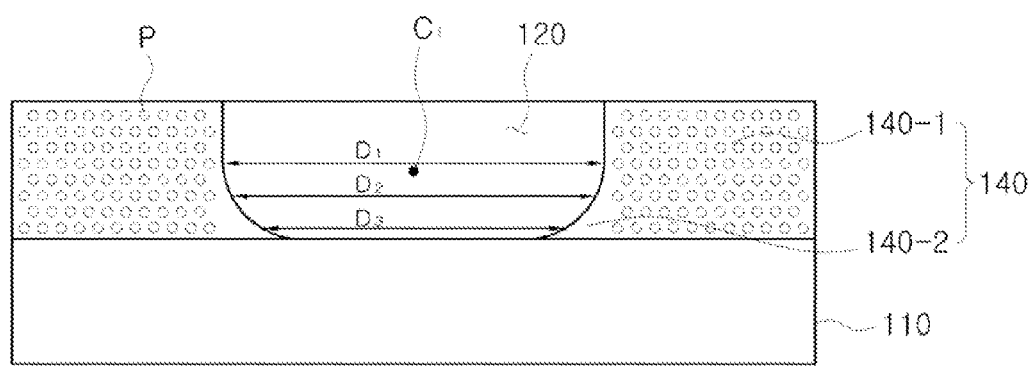
FIG. 2 is a cross-sectional view taken along line AA' of the optical analysis structure of FIG. 1.
Figure 3:
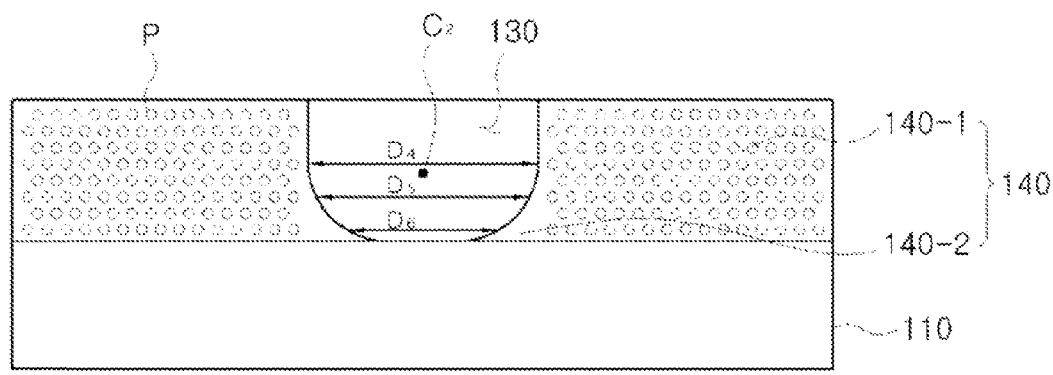
FIG. 3 is a cross-sectional view taken along line BB' of the optical analysis structure of FIG. 1.

FIG. 1 is a perspective view illustrating an optical analysis structure 100 according to an exemplary embodiment, and FIG. 2 is a cross-sectional view taken along line AA' of the optical analysis structure 100 of FIG. 1, and FIG. 3 is a cross-sectional view taken along line BB' of the optical analysis structure 100 of FIG. 1.

Referring to FIGS. 1, 2, and 3, an optical analysis structure 100 according to an exemplary embodiment may include a support 110 and an ink structure 140 coupled to the support 110 to form a chamber 120 and a channel 130 on one surface of the support 110.

The support 110 may be provided to support the ink structure 140. The support 110 may be provided, for example, in one of a thin film shape of a film-type and a flat shape. Meanwhile, the support 110 may be provided in a curved shape, and include a hydrophilic surface coupled to the ink structure 140 according to an exemplary embodiment.

The ink structure 140 may be formed by coating an ink composition having a pigment-based ink and a resin-based ink.

The ink composition may include the pigment-based ink that comprises between 30% and 70% of a total weight of the ink composition, and the resin-based ink that comprises between 30% and 70% of the total weight of the ink composition. According to an exemplary embodiment, the ink composition may further include a curing agent and a retardant that jointly comprise between 10% and 20% of the total weight of the ink composition. Generally, since the pigment-based ink includes, as a constituent thereof, the resin-based ink at between 5% and 15% of the total weight of the pigment-based ink, the ink composition may include the pigment-based ink at between 20.4% and 59.85%, the resin-based ink at between 25.2% and 72.45%, and the combination of the curing agent and the retardant at between 10% and 20% of the total weight of the ink composition, when the ink composition further includes the curing agent and the retardant. The composition ratio of the ink composition is not limited thereto, and may be appropriately adjusted according to necessity.

When the ink structure 140 is formed and the proportion of the pigment-based ink included in the ink composition is excessively high, a phenomenon in which a sample is absorbed into holes formed between pigment particles P may occur, and a hydrophobic property may vary according to a curing temperature. Conversely, when the proportion of the resin-based ink is excessively high, a corner of the structure may collapse, and thus, it is not easy to manufacture the ink structure 140 so as to have an accurate size, and a solvent injected into the structure consequently may overflow to outside the structure.

By contrast, when the ink structure 140 is formed of an ink composition including a pigment-based ink and a resin-based ink, a structure in which the resin-based ink fills between the pigment particles P may be formed, and thus, a sample that passes through the structure may be safely transported and uniform optical measurement data may be simultaneously obtained. Hereinafter, related parts will be described.

The pigment-based ink may include one or more selected from among rutile, anatase, antimony oxide, zinc, calcium carbonate, silica, cadmium, chromium, cobalt, copper, iron oxide, lead, manganese, mercury, titanium, carbon, clay earth, ultramarine, alizarin, alizarin crimson, gamboge, cochineal red, rose madder, indigo, indian yellow, tyrian purple, quinacridone, magenta, phthalo green phthalo blue pigment red 170, and diarylide yellow.

In addition, the resin-based ink may include one or more selected from among silicone, cryptal, a semiconductor, benzoin, petroleum, styrene, aniline, an amino group, amino alkyd, vinyl acetate, alkyd, epoxy, urea, a casting resin, toluene, plastic, polyamide, polyurethane, and amber.

The ink structure 140 is coupled to the support 110 and may form the chamber 120 and the channel 130 on one surface of the support 110. Referring to FIGS. 2 and 3, the ink structure 140 may include a first ink structural component 140-1 which forms the body of the ink structure 140 and a second ink structural component 140-2 disposed on an lower portion of a side surface of the first ink structural component 140-1 and having a different slope than the first ink structural component 140-1 in a direction of a center C1 or C2 of the chamber 120 or the channel 130, and the chamber 120 and the channel 130 may be formed by the first ink structural component 140-1 and the second ink structural component 140-2. Even though the first ink structural component 140-1 and the second ink structural component 140-2 are divided for the sake of convenience in the description, as illustrated in FIGS. 2 and 3, the first ink structural component 140-1 and the second ink structural component 140-2 may have a smoothly connected structure.

The chamber 120 refers to a space configured to accommodate a sample. According to an exemplary embodiment, a reagent may be accommodated in the chamber 120 in advance, and in this case, a reaction of an injected sample and the reagent may be monitored by optical analysis. As illustrated in FIG. 2, the chamber 120 may be provided with decreasing diameters from the starting point of the second ink structure 140-2 in a direction of the support 110. In particular, a relation may be $D_1 > D_2 > D_3$, where, $D_1$, $D_2$, and $D_3$ refer to respective diameters of the chamber 120 in the direction of the support 110.

The channel 130 refers to a path of movement of the injected sample, and may have a width of between several micrometers (μm) and several hundred μm. Thus, the injected sample may move to the chamber 120 due to the capillary force of the channel 130. As illustrated in FIG. 3, the channel 130 may be provided with decreasing diameters from the starting point of the second ink structural component 140-2 in a direction of the support 110. In particular, the relation may be $D_4 > D_5 > D_6$, where, $D_4$, $D_5$, and $D_6$ refer to the diameters of the channel 130 in the direction of the support 110.

The first ink structural component 140-1 that forms the body of the ink structure 140 may be formed of the pigment-based ink and the resin-based ink. More particularly, the first ink structural component 140-1 may be coated with the ink composition described above, and may have the same composition ratio as the ink composition described above, within an error range generated during a curing process.

The second ink structural component 140-2 may be formed of a resin-based ink. More particularly, the second ink structural component 140-2 may be formed by a part of the resin-based ink included in the ink composition flowing downward due to gravity. The slope of the longitudinal section of the second ink structural component 140-2 may decrease in the direction of the support 110, and the longitudinal section may have a parabolic shape or a Gaussian distribution shape according to an exemplary embodiment.

Figure 4:
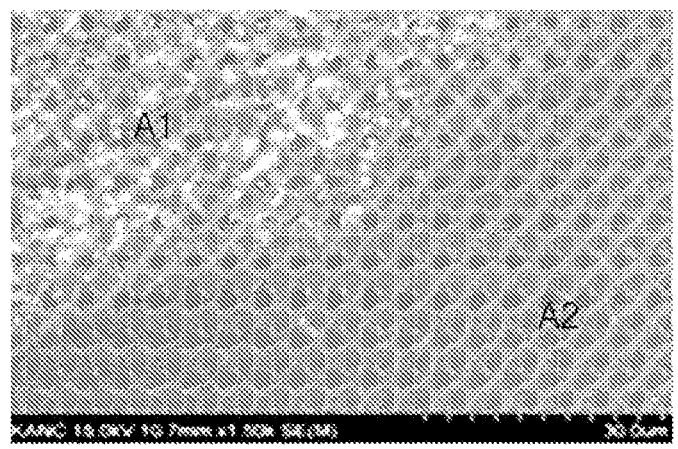
FIG. 4 is a scanning electron microscope (SEM) image of a cross section of an ink structure formed of a pigment-based ink and a resin-based ink.

To facilitate understanding, in the accompanying FIG. 4, a scanning electron microscope (SEM) image of a cross section of the ink structure 140 formed of a pigment-based ink and a resin-based ink is provided. An area A1 of FIG. 4 is the SEM image of a cross-section of the first ink structural component 140-1, and an area A2 is the SEM image of a cross-section of the second ink structural component 140-2.

Referring to FIG. 4, the first ink structural component 140-1 may be provided in a shape in which the resin-based ink fills spaces between the pigment particles P, and the type of the structure may prevent a phenomenon in which a sample permeates a wall surface of the ink structure 140. In addition, the ink structure 140 that has an accurate size may be formed by solidly forming the ink structure 140 using the pigment particle P.

Figure 5:
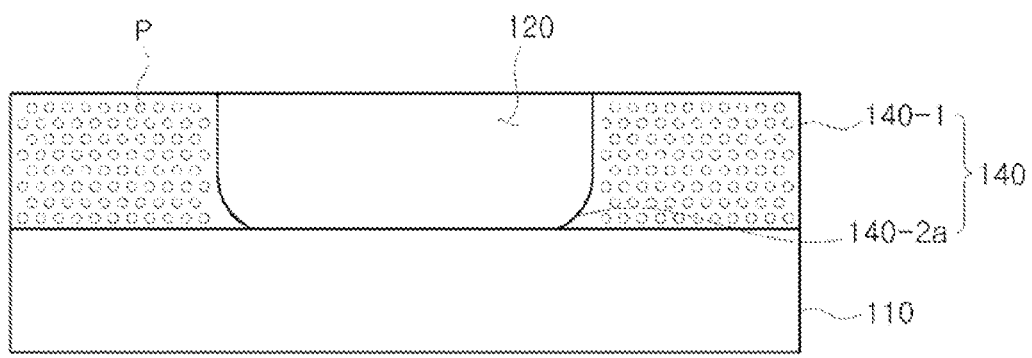
FIG. 5 is a cross-sectional view illustrating another example of an optical analysis structure.
Figure 6:
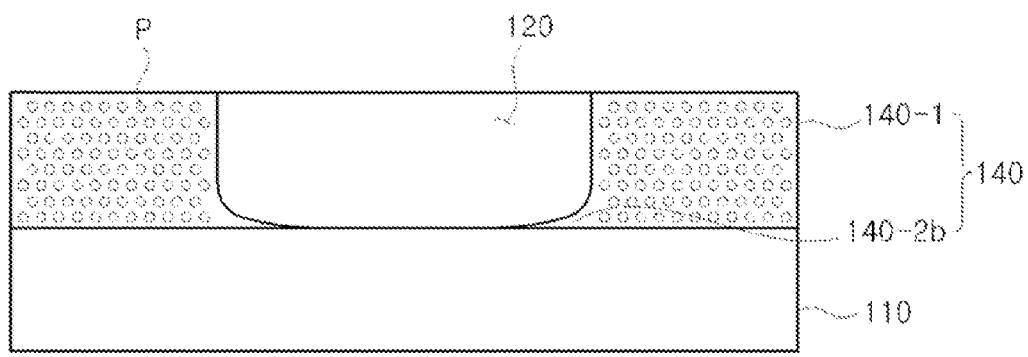
FIG. 6 is a cross-sectional view illustrating still another example of an optical analysis structure.

The various shapes of the longitudinal section of the ink structure 140 may be provided according to one or more of a composition ratio, a curing temperature, and a curing time of a provided ink. FIG. 5 is a cross-sectional view illustrating another example of an optical analysis structure 100, and FIG. 6 is a cross-sectional view illustrating still another example of an optical analysis structure 100. In FIGS. 5 and 6, the cross-sections of the chamber 120 are illustrated for the sake of convenience in the description.

Referring to FIG. 5, a second ink structural component 140-2a disposed on an edge of the chamber 120 of the optical analysis structure 100 may have a steeper slope than the second ink structural component 140-2 illustrated in FIG. 2. Conversely, referring to FIG. 6, a second ink structural component 140-2b of the optical analysis structure 100 may have a more gradual (i.e., less steep) slope than the second ink structural component 140-2 illustrated in FIG. 2. In particular, the second ink structural component 140-2 may be formed so that a longitudinal section may have various slopes, and include changes within a range which may be easily considered by those of skill in the art.

The first ink structural component 140-1 and the second ink structural component 140-2 may have different hydrophilicity/lipophilicity. More particularly, the second ink structural component 140-2 has a higher lipophilicity than the first ink structural component 140-1, and in other words, the second ink structural component 140-2 may have a lower hydrophilic property than the first ink structural component 140-1.

Hydrophilicity/lipophilicity of the first ink structural component 140-1 and the second ink structural component 140-2 may be important in determining the flowability of a sample accommodated in the chamber 120 and/or the channel 130. Thus, hydrophilicity/lipophilicity of the ink structure 140 according to a type of the sample and the spreadability aspect of the sample according to sample injection will be described before the flowability of the sample is described.

Hydrophobicity refers to a lack of affinity for water, and lipophilicity denotes a high affinity for oil. In this regard, the hydrophobic property and the lipophilicity of a specific solvent may appear in the same aspect, and hereinafter, a description of the lipophilicity may include a description of the hydrophobicity.

In order to determine the hydrophilicity/lipophilicity of an ink structure 140, an experiment in which an organic solvent and a hydrophilic buffer are dropped on various types of the ink structures 140 is performed.

When an organic solvent is dropped on an ink structure 140, an organic solvent drop may be formed on a surface thereof. The organic solvent is an organic chemical substance in a liquid state and may dissolve oil and the like, and has a greater affinity for a lipophilic surface than for a hydrophilic surface. Thus, the spreadability of the organic solvent on the surface of the ink structure 140 where the organic solvent is dropped may be increased when the surface of the ink structure 140 is lipophilic. In particular, the radius of the organic solvent drop may be formed so as to be greater when the surface of the ink structure 140 is lipophilic.

Figure 7:
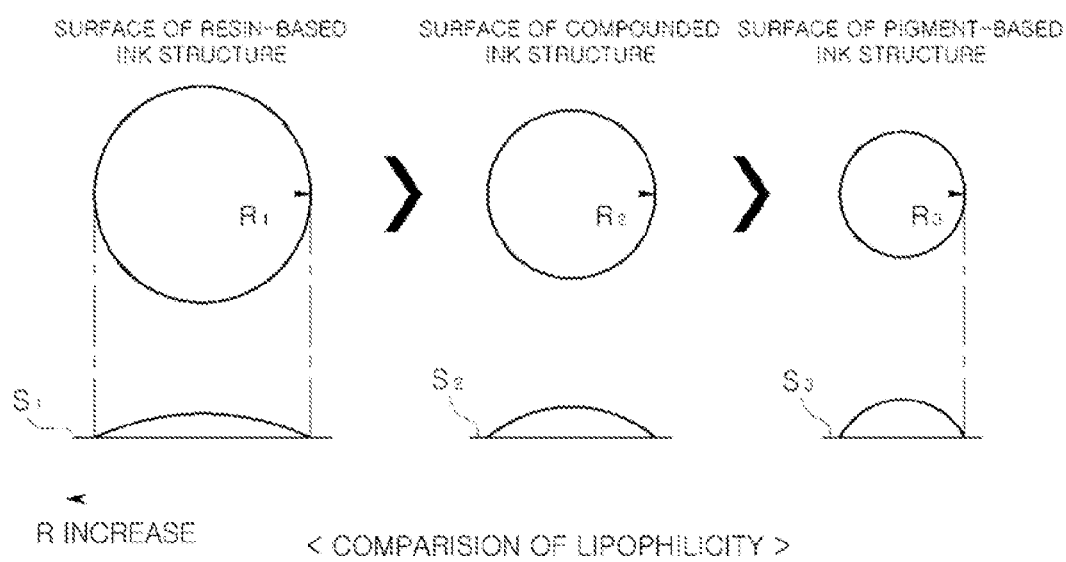
FIG. 7 is a comparative view illustrating a case when organic solvents are dropped on an ink structure.

In FIG. 7, the result of dropping an organic solvent on a surface $S_1$ of a resin-based ink structure, a surface $S_2$ of a compound structure in which the resin-based ink and a pigment-based ink are mixed, and a surface $S_3$ of the pigment-based ink structure is illustrated, and here, 0.42 µl of cyclohexanone is used as the organic solvent.

As a result of the experiment, an organic solvent drop having a radius $R_1$ of about 0.547 mm was formed on the surface $S_1$ of the resin-based ink structure, and an organic solvent drop having a radius $R_2$ of about 0.521 mm was formed on the surface $S_2$ of the compound structure, and an organic solvent drop having a radius $R_3$ of about 0.471 mm was formed on the surface $S_3$ of the pigment-based ink structure. In this aspect, it was determined that the radius $R_1$ of the organic solvent formed on the surface $S_1$ of the resin-based ink structure is the greatest ($R_1 > R_2 > R_3$), as the result of the experiment, and thus, the surface $S_1$ of the resin-based ink structure had the greatest lipophilicity.

Next, when a water-soluble buffer is dropped on the ink structure 140, a water-soluble buffer drop may be formed on a surface thereof. The water-soluble solvent is a liquid state substance having a high affinity for water, and has a greater affinity for a hydrophilic surface than a lipophilic surface. Thus, the spreadability of the water-soluble buffer on the surface of the ink structure 140 where the water-soluble buffer is dropped may be increased when the surface of the ink structure 140 is hydrophilic. In particular, the radius of water-soluble buffer drop may be formed so as to be greater when the surface of the ink structure 140 is hydrophilic.

Figure 8:
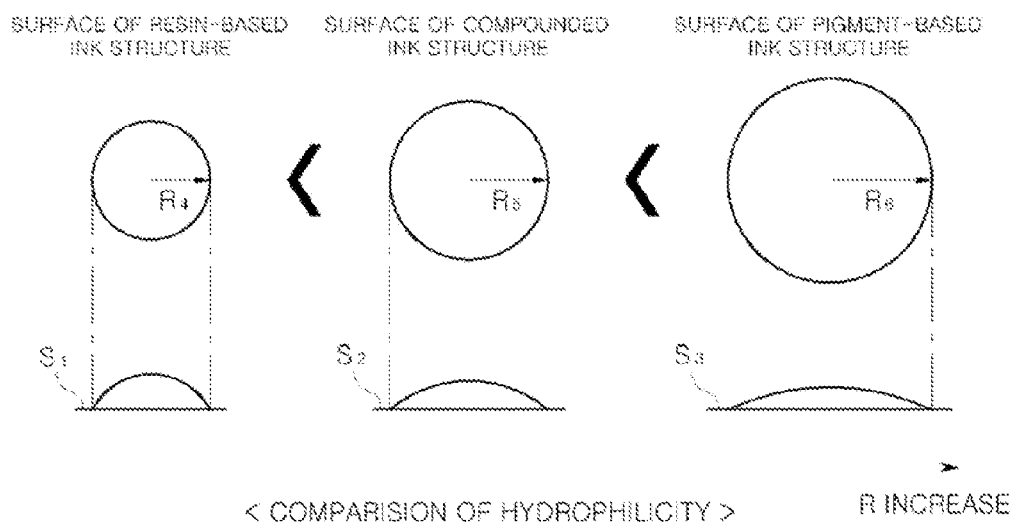
FIG. 8 is a comparative view illustrating a case when water-soluble buffers are dropped on an ink structure.

In FIG. 8, a result of dropping the water-soluble buffer on a surface $S_1$ of a resin-based ink structure, a surface $S_2$ of a compounded structure in which the resin-based ink and a pigment-based ink are mixed, and a surface $S_3$ of the pigment-based ink structure is illustrated, and here, 0.42 µl of the water-soluble buffer is respectively dropped on each surface.

As a result of the experiment, a water-soluble buffer drop having a radius $R_4$ of about 0.393 mm was formed on the surface $S_1$ of the resin-based ink structure, and an water-soluble buffer drop having a radius $R_5$ of about 0.546 mm was formed on the surface $S_2$ of the compounded structure, and an water-soluble buffer drop having a radius $R_6$ of about 0.562 mm was formed on the surface $S_3$ of the pigment-based ink structure. In this aspect, it was determined that the radius $R_6$ of the water-soluble buffer formed on the surface $S_3$ of the resin-based ink structure is the greatest ($R_6 > R_5 > R_4$), as the result of the experiment, and thus, the surface $S_3$ of the pigment-based ink structure had the greatest hydrophilicity.

Meanwhile, when the results of FIGS. 7 and 8 are summarized, in the organic solvent case, the organic solvent drop having a radius of about 0.521 mm ($R_2$=0.521 mm) was formed on the surface $S_2$ of the compounded structure, and in the water-soluble buffer case, the water-soluble buffer drop having a radius of about 0.546 mm ($R_5$=0.546 mm) was formed on the surface $S_2$ of the compounded structure. That is, it was determined that the spreadabilities of the organic solvent and the water-soluble solvent on the surface $S_2$ of the compounded structure are similar to each other.

Next, the spreadability aspect of the sample will be described based on the lipophilicity/hydrophilicity of the ink structure 140 according to a sample injection.

Figure 9:
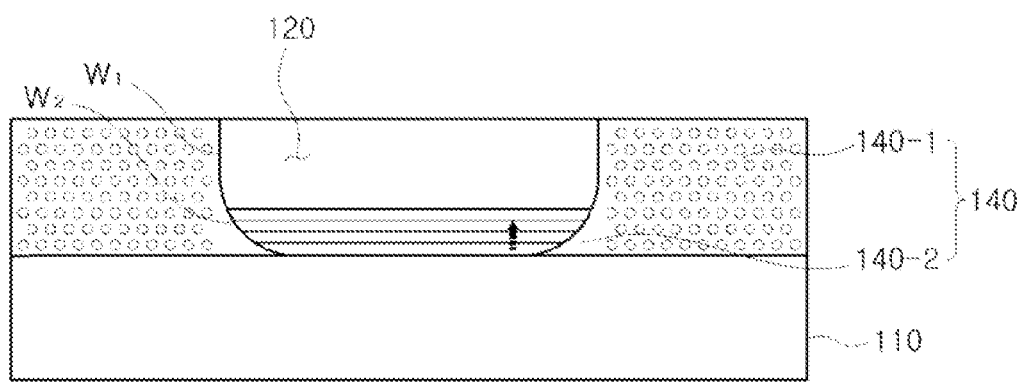
FIGS. 9 and 10 are views illustrating the spreadability of an organic solvent when the organic solvent is dropped into a chamber.
Figure 10:
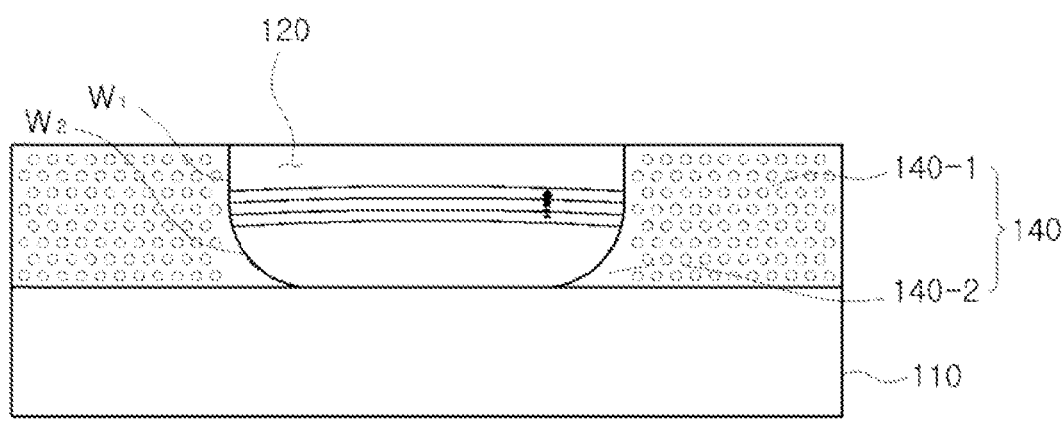
Figure 11:
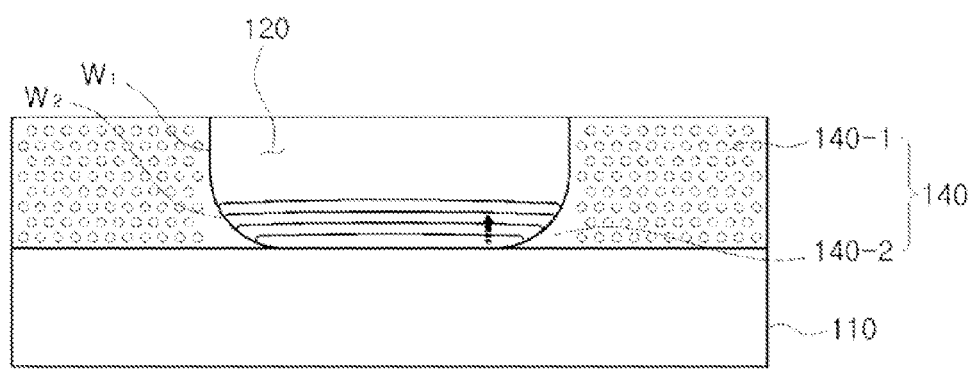
FIGS. 11 and 12 are views illustrating the spreadability of a water-soluble buffer when the water-soluble buffer is dropped into a chamber.
Figure 12:
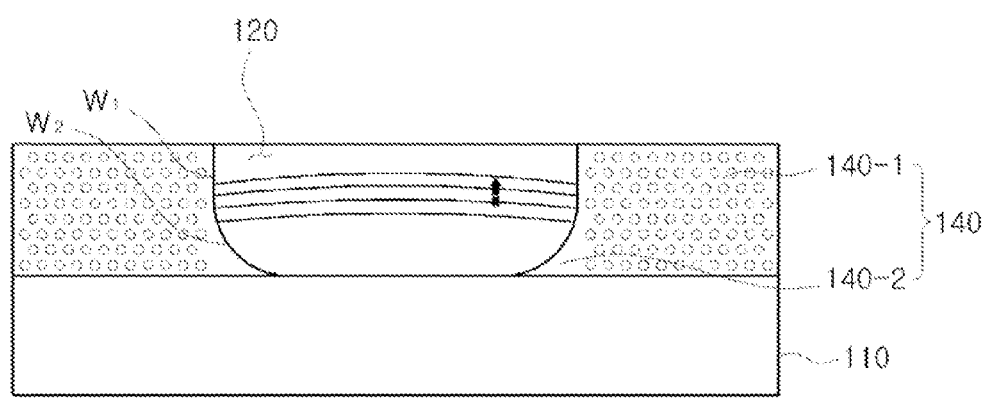

FIGS. 9 and 10 are views illustrating the spreadability of an organic solvent when the organic solvent is dropped into a chamber 120. FIGS. 11 and 12 are views illustrating the spreadability of a water-soluble buffer when the water-soluble buffer is dropped into a chamber 120. However, in FIGS. 9, 10, 11, and 12, even though the chamber 120 is described as an example, the same principle may be applied to a channel 130.

A case in which an organic solvent is dropped into a chamber 120 will be described first.

Referring to FIGS. 9 and 10, a chamber 120 may include a first sidewall $W_1$ formed by a first ink structural component 140-1, and a second sidewall $W_2$ formed by a second ink structural component 140-2. Here, since the first ink structural component 140-1 is a compounded ink structure 140 and the second ink structural component 140-2 is a resin-based ink structure 140, the first ink structural component 140-1 may have a lower lipophilicity than the second ink structural component 140-2. In particular, an organic solvent may have a greater affinity with the second sidewall $W_2$ than with the first sidewall $W_1$.

When the organic solvent is dropped into the chamber 120, the organic solvent is in contact with the second sidewall $W_2$ adjacent to a support 110, as illustrated in FIG. 9. At this time, the organic solvent has high spreadability due to the affinity between the organic solvent and the second sidewall $W_2$. As a result, the dropped organic solvent spreads relatively uniformly on the inside of the chamber 120 formed by the second sidewall $W_2$.

When the organic solvent is continuously dropped into the chamber 120, the organic solvent is in contact with the first sidewall $W_1$. At this time, since the first sidewall $W_1$ has a lower affinity for the organic solvent than the second sidewall $W_2$, the spreadability of the organic solvent is decreased compared to a case illustrated in FIG. 9. As a result, as illustrated in FIG. 10, the dropped organic solvent may be spread in a more convex shape than the case illustrated in FIG. 9.

In summary, the organic solvent may have a spreadability at the contact surface of the second sidewall $W_2$ that is greater than spreadability at the contact surface of the first sidewall $W_1$. Thus, since the organic solvent has relatively high spreadability at the contact surface of the second sidewall $W_2$, a uniform result value may be derived in an optical analysis. In addition, since the organic solvent may comparatively have a lower spreadability at the contact surface of the first sidewall $W_1$, the phenomenon in which the organic solvent overflows out of the chamber 120 may be prevented.

Next, the case in which a water-soluble buffer is dropped into a chamber 120 will be described.

Referring to FIGS. 11 and 12, a chamber 120 may include a first sidewall $W_1$ formed by a first ink structural component 140-1, and a second sidewall $W_2$ formed by a second ink structural component 140-2 as illustrated in FIGS. 9 and 10. Since the first ink structural component 140-1 is a compounded ink structure 140 and the second ink structural component 140-2 is a resin-based ink structure 140, the first ink structural component 140-1 may have a higher hydrophilicity than the second ink structural component 140-2. In particular, a water-soluble buffer may have a greater affinity for the first sidewall $W_1$ than for the second sidewall $W_2$.

When a water-soluble buffer is dropped into a chamber 120, the water-soluble buffer is in contact with a second sidewall $W_2$ adjacent to a support 110, as illustrated in FIG. 11. As described above, since the second sidewall $W_2$ has a resin-based structure and high lipophilicity, the dropped water-soluble buffer has a comparatively high contact angle with the second sidewall $W_2$ and is accommodated inside the chamber 120.

When the water-soluble buffer continuously is dropped into the chamber 120, the water-soluble buffer is in contact with the first sidewall $W_1$. At this time, since the first sidewall $W_1$ has a greater affinity for the water-soluble buffer than the second sidewall $W_2$, the spreadability of the water-soluble buffer is increased compared to the case illustrated in FIG. 11. In particular, as illustrated in FIG. 12, the dropped water-soluble buffer has a comparatively lower contact angle with a bottom surface, and is spread on an inside of the chamber 120.

In summary, the water-soluble buffer may have a greater spreadability at a contact surface of the first sidewall $W_1$ than spreadability at a contact surface of the second sidewall $W_2$. In particular, in the water-soluble buffer case, since the spreadability of the solution may be increased by the first sidewall $W_1$, a uniform result value may be derived in optical analysis. In addition, since the water-soluble buffer is provided to have appropriate spreadability due to the first sidewall $W_1$, a phenomenon in which the water-soluble buffer overflows out of the chamber 120 may be prevented.

The ink structure 140 described above may be provided in any of various shapes.

FIGS. 13, 14, 15, and 16 are perspective views illustrating optical analysis structures 100a, 100b, 100c, and 100d according to various exemplary embodiments.

Figure 13:
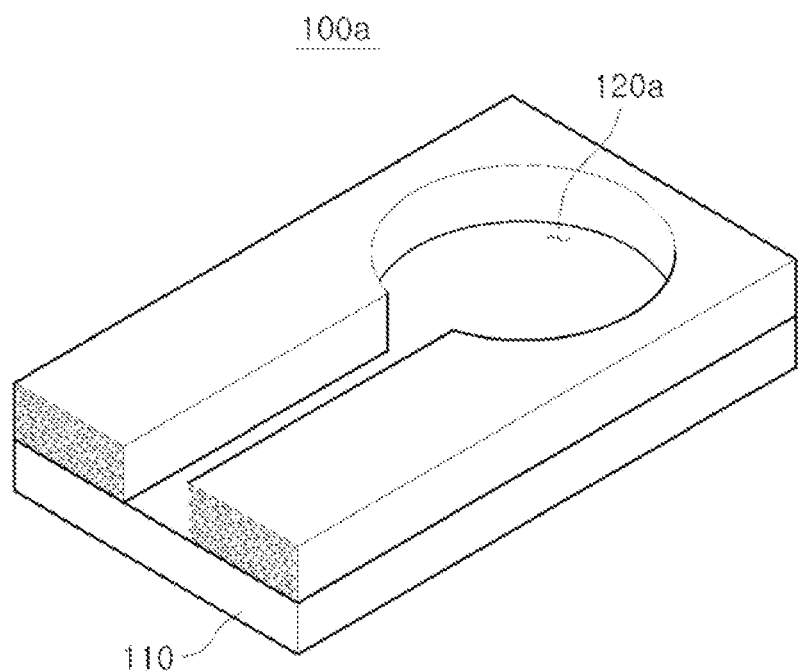
FIGS. 13, 14, 15, and 16 are perspective views illustrating various exemplary embodiments of an optical analysis structure.
Figure 14:
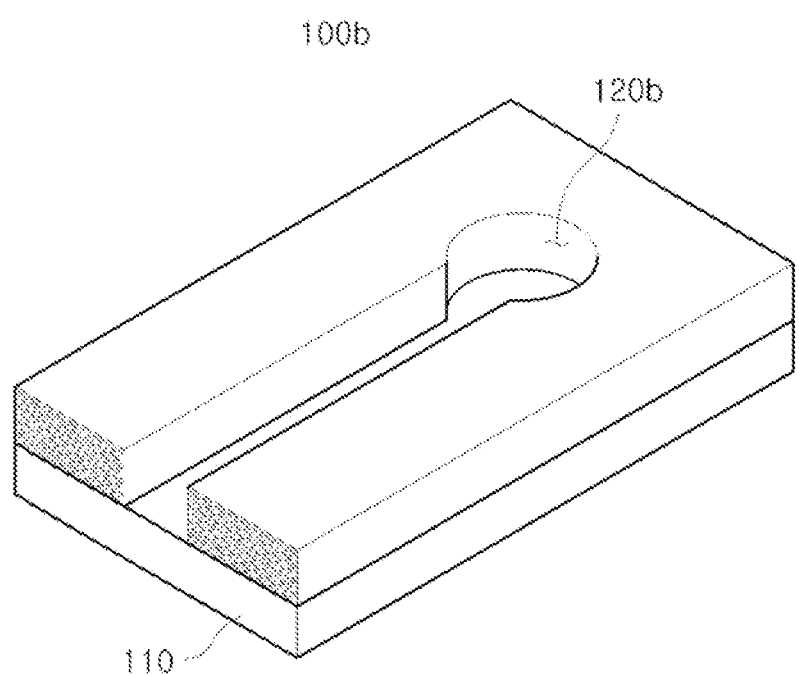

The optical analysis structures 100a and 100b may include chambers 120a and 120b having various sizes. An optical analysis structure 100a according to one exemplary embodiment may have a chamber 120a having a relatively large radius, as illustrated in FIG. 13, and an optical analysis structure 100b according to another exemplary embodiment may have a chamber 120b having a relatively small radius, as illustrated in FIG. 14. Thus, the amount of a sample may be adjusted by varying the sizes of the chambers 120a and 120b formed on the optical analysis structures 100a and 100b.

Figure 15:
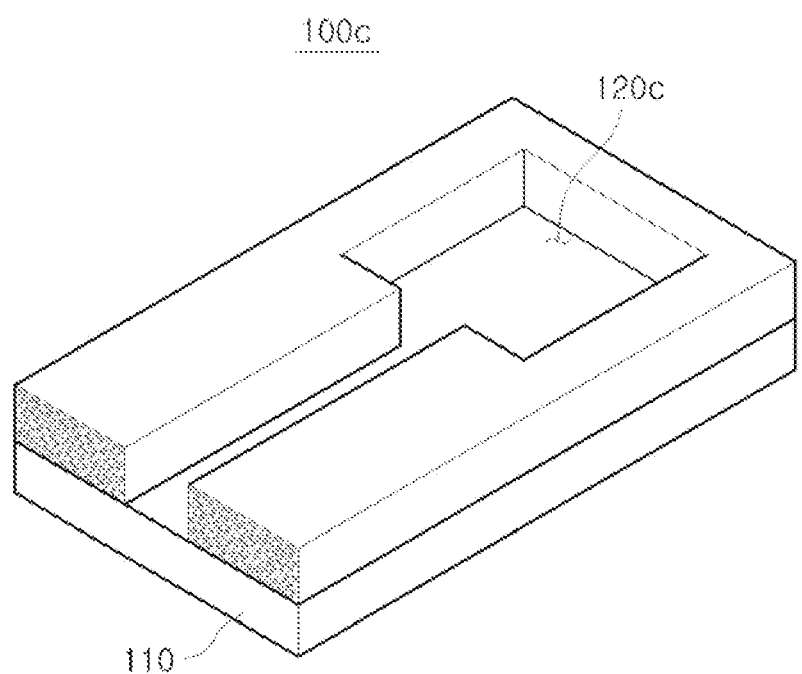

An optical analysis structure 100c may include a chamber 120c having one of various shapes. An optical analysis structure 100c according to one exemplary embodiment may include a chamber 120c having a rectangular shape, as illustrated in FIG. 15. The shape of the chamber 120c is not limited thereto, and includes changes within a range which may be easily considered by those of skill in the art.

Figure 16:
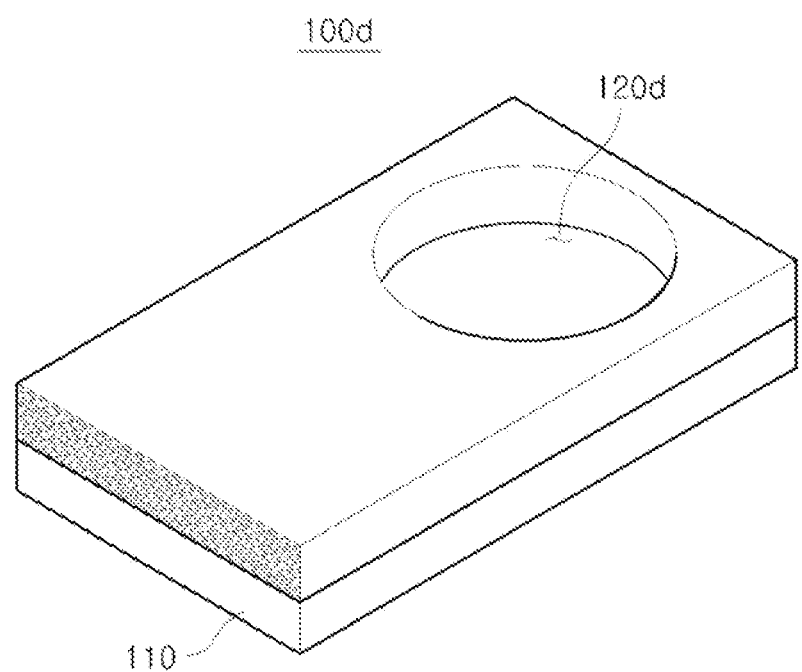

Further, an optical analysis structure according to an exemplary embodiment may only include a chamber. Referring to FIG. 16, an optical analysis structure 100d according to one exemplary embodiment may include a chamber 120d having a circular shape, and may not additionally include a channel. In this case, a sample may be directly injected into the chamber 120d. In addition, the optical analysis structure 100d according to an exemplary embodiment may include a chamber 120d having any of various sizes and shapes.

When the optical characteristic of a sample is measured using the optical analysis structures 100, 100a, 100b, 100c, and 100d described above, a dispersion value as described below may be shown. Hereinafter, the optical analysis structure 100 in FIG. 1 will be described as a typical example.

Figure 17:
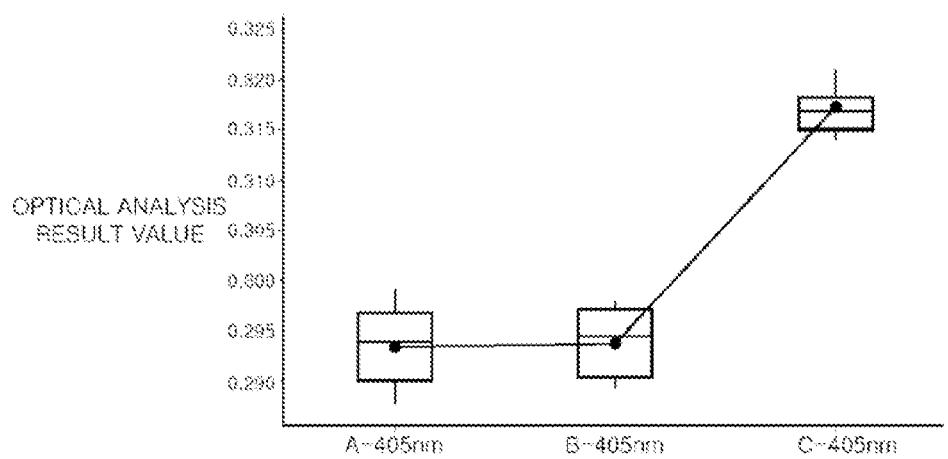
FIGS. 17, 18, 19, and 20 are candlestick charts illustrating dispersions of measurement values when optical characteristics of samples are examined using the optical analysis structure, according to an exemplary embodiment.
Figure 18:
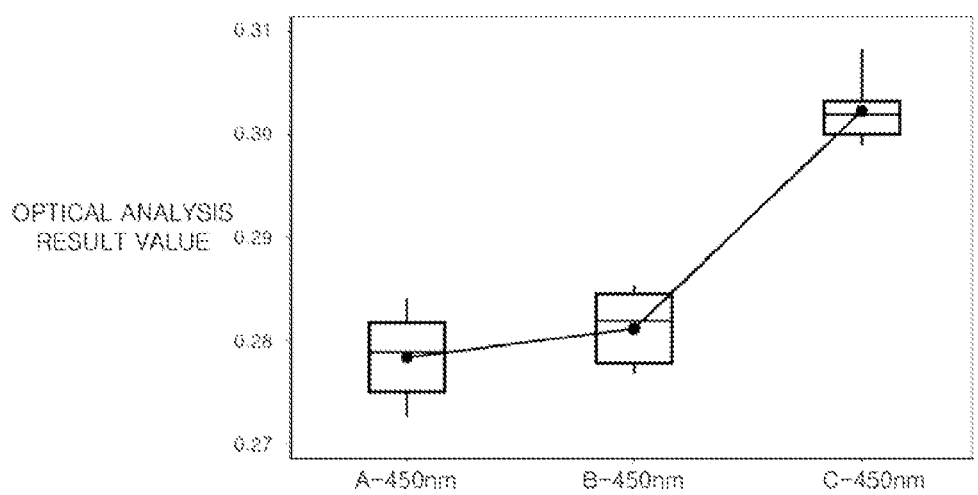
Figure 19:
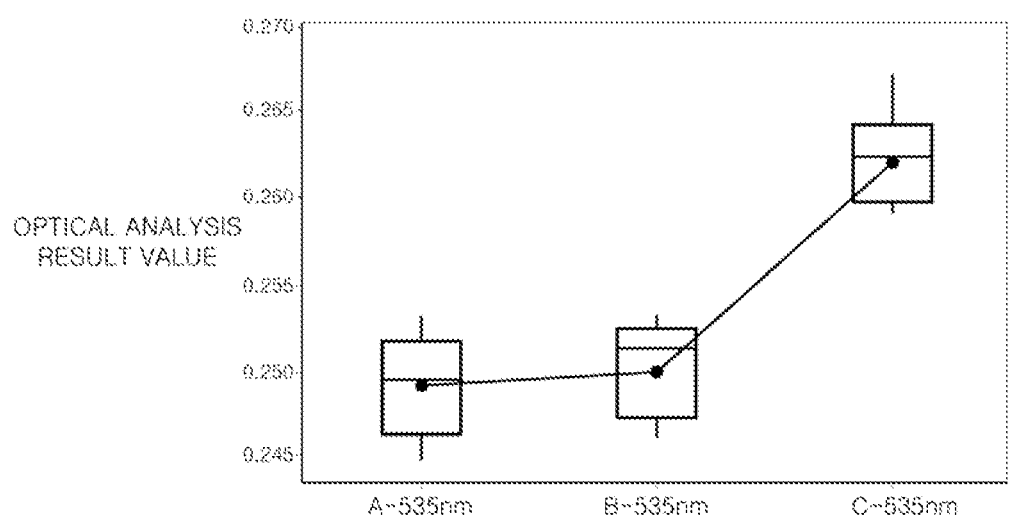
Figure 20:
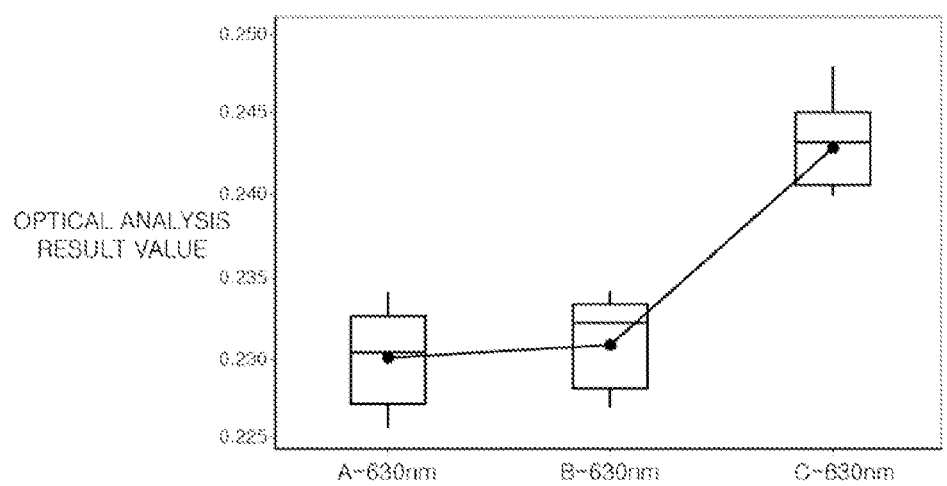
Figure 21A:
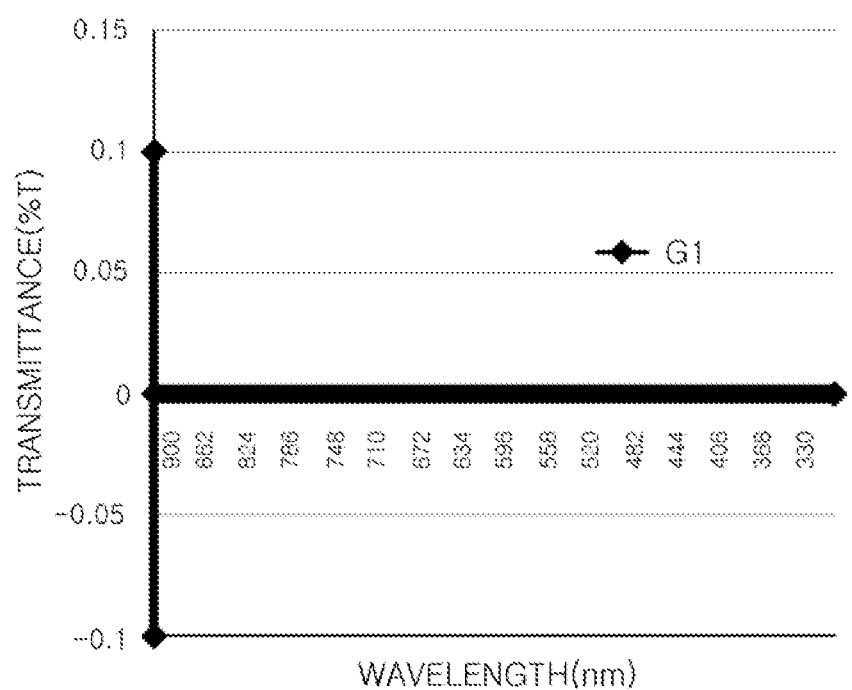
FIGS. 21A, 21B, 21C, 21D, 21E, 21F, and 21G are graphs illustrating transmittance values according to the amounts of the types of inks included in an ink composition.
Figure 21B:
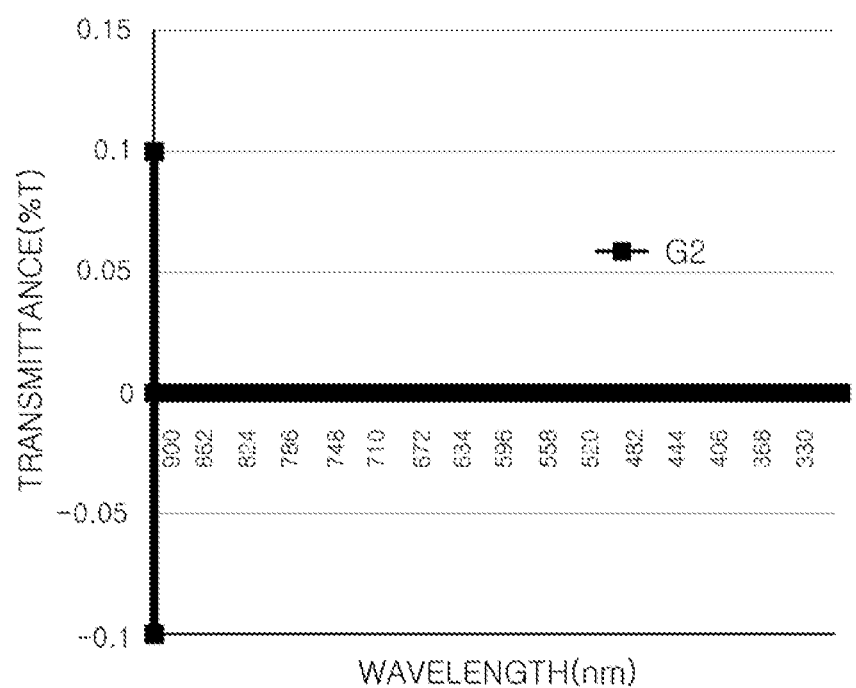
Figure 21C:
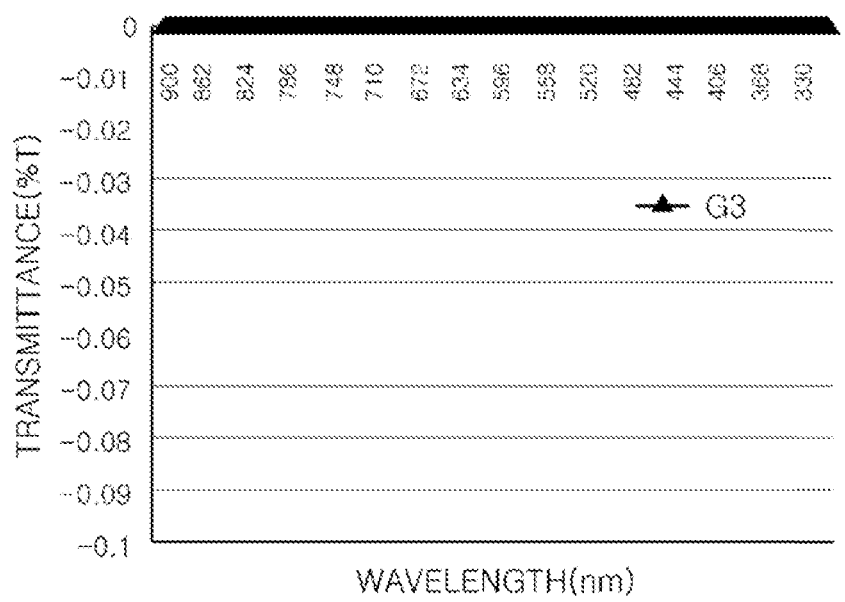
Figure 21D:
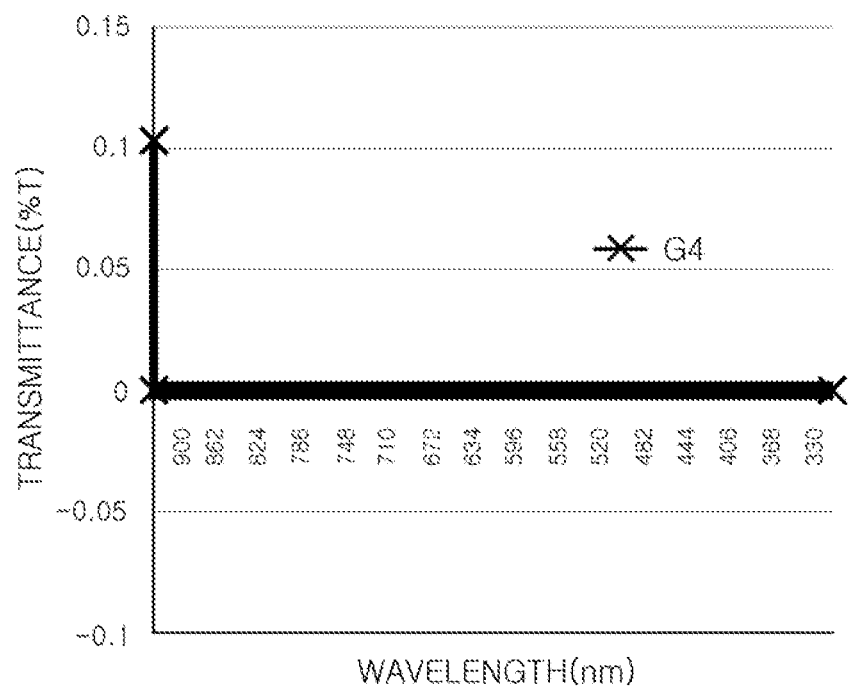
Figure 21E:
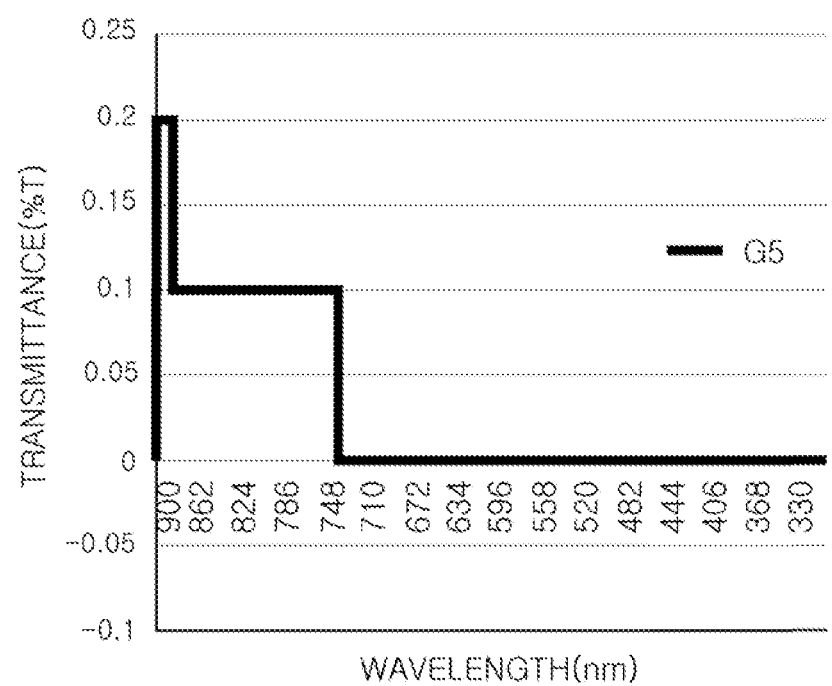
Figure 21F:
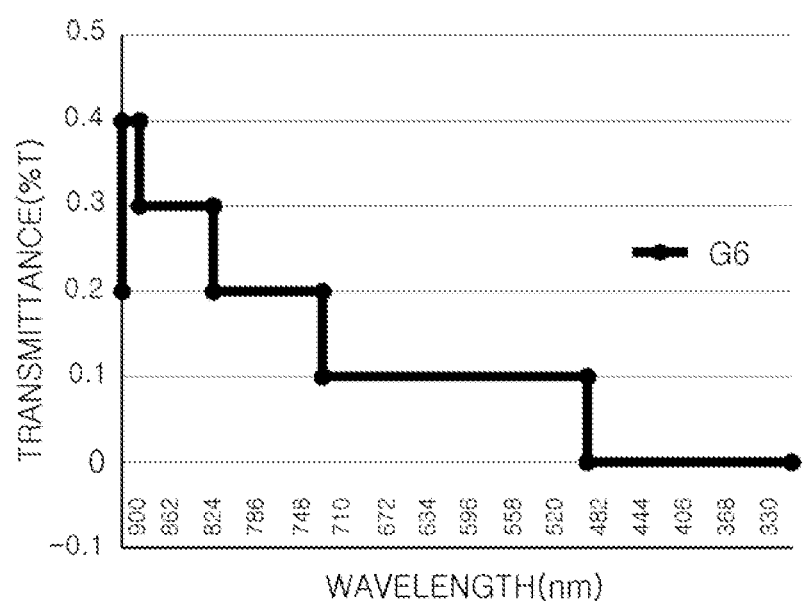
Figure 21G:
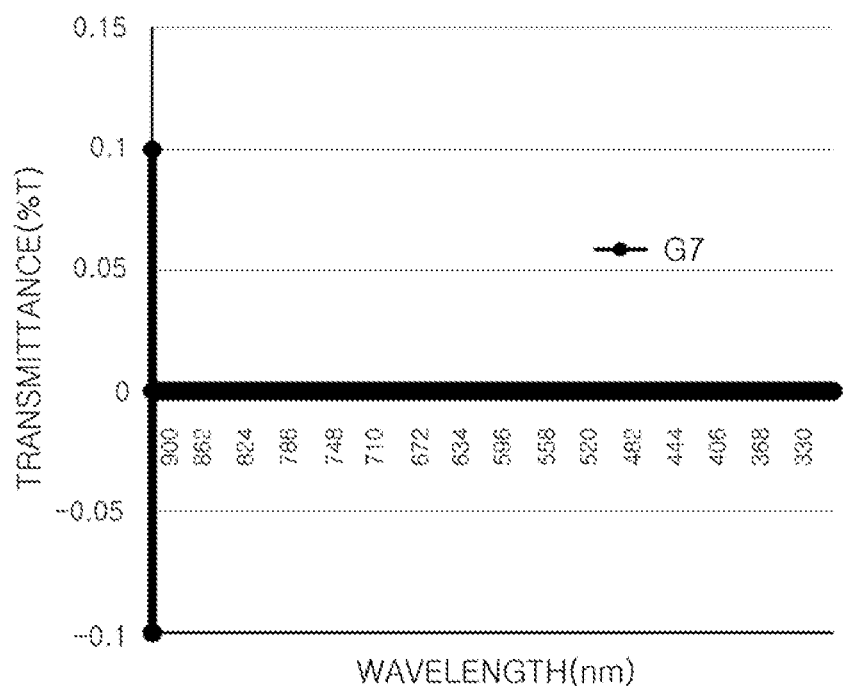

FIGS. 17, 18, 19, and 20 are candlestick charts illustrating dispersions of measuring values when optical characteristics of samples are measured using the optical analysis structure 100 according to an exemplary embodiment. More particularly, FIG. 17 is a candlestick chart illustrating the dispersions of a sample at a 405 nm wavelength, FIG. 18 is a candlestick chart illustrating the dispersions of a sample at a 450 nm wavelength, FIG. 19 is a candlestick chart illustrating the dispersions of a sample at a 535 nm wavelength, and FIG. 20 is a candlestick chart illustrating the dispersions of a sample at a 630 nm wavelength.

In FIGS. 17, 18, 19, and 20, A, B, and C on horizontal axes respectively refer to a pigment-based ink structure, a resin-based ink structure, and a compounded ink structure, and vertical axes refers to optical analysis result values. Referring to FIGS. 17, 18, 19, and 20, it is determined that the dispersions of optical analysis result values are relatively large when samples are optically analyzed using the pigment-based ink structure and the resin-based ink structure. More particularly, referring to FIG. 17, it is determined that the optical analysis result values of samples range from about 0.290 to 0.297 when samples are optically analyzed using a pigment-based ink structure, and it is determined that optical analysis result values of samples range from about 0.291 to 0.297 when samples are optically analyzed using a resin-based ink structure. By contrast, it is determined that optical analysis result values of samples range from about 0.315 to 0.318 when samples are optically analyzed using a compounded ink structure. In particular, it is determined that the dispersion of the optical analysis result value is relatively lower when the compounded structure is used. As a result, it is determined that a compounded structure shows an optimum performance as an optical analysis structure.

Next, the transmittance of an optical analysis structure 100 will be described.

In the optical analysis structure 100 described above, the light transmittance of an ink structure 140 may be adjusted by adjusting a type of an ink composition forming the ink structure 140 and the composition ratio of inks included in the ink composition. More particularly, the light transmittance of the ink structure 140 may be increased as the composition ratio of a white resin-based ink in the ink composition is increased.

Hereinafter, the term "white resin-based ink" refers to a resin-based ink having a pigment-based ink configured to implement white color, and "black resin-based ink" refers to a resin-based ink having a pigment-based ink configured to implement black color, and "black pigment-based ink" refers to a pigment-based ink mostly having a pigment-based ink configured to implement black color. A pigment configured to implement white color may include, for example, any of titanium oxide, zinc oxide, zinc sulfide, and lead oxide, and a pigment configured to implement black color may include carbon and the like.

Meanwhile, an example of adjusting the light transmittance is not limited thereto, and the assembly of optical analysis structures having various light transmittance qualities is provided by compounding a pigment-based ink having one of various colors and a resin-based ink having one of various colors according to an exemplary embodiment.

FIGS. 21A, 21B, 21C, 21D, 21E, 21F, and 21G are graphs showing light transmittance values according to the amounts of types of ink included in an ink composition.

In FIGS. 21A, 21B, 21C, 21D, 21E, 21F, and 21G, the horizontal axes of graphs refer to the wavelength of incident light, and the vertical axes refer to the transmittances of the light. In addition, FIGS. 21A, 21B, 21C, 21D, 21E, 21F, and FIG. 21G illustrate the light transmittance of ink structures 140 including an ink composition G1 having only a black resin-based ink, an ink composition including a black pigment-based ink compounded with a white resin-based ink at the following ratios: a ratio of 9:1 for ink composition G2, a ratio of 8:2 for ink composition G3, a ratio of 7:3 for ink composition G4, at ratio of 6:4 for ink composition G5, and at ratio of 5:5 for ink composition G6, and an ink composition G7 having only a white pigment-based ink.

As an experimental result, the ink structure 140 showed a light transmittance in a range of about −0.1% to 0.1% in the case G1 of the ink composition having the black resin-based ink, the ink structure 140 showed a light transmittance in a range of about −0.1% to 0.1% in the case G2 of the ink composition having a black pigment-based ink compounded with white resin-based ink at the ratio 9:1, the ink structure 140 showed a light transmittance of about zero percent (0%) in the case G3 of the compounded ratio of 8:2, the ink structure 140 showed a light transmittance in a range of about 0% to 0.1% in the case G4 of the compounded ratio of 7:3, the ink structure 140 showed a light transmittance in a range of about 0% to 0.2% in the case G5 of the compounded ratio of 6:4, the ink structure 140 showed a light transmittance in a range of about 0% to 0.4% in the case G6 of the ratio of 5:5, and the ink structure 140 showed a light transmittance in a range of about −0.1% to 0.1% in the case G7 of the ink composition having the white resin-based ink.

In this aspect, it is determined that the light transmittance of the ink structure 140 generally increases as a composition ratio of the white resin-based ink is increased.

Meanwhile, in the ink structure 140 according to an exemplary embodiment, the transmittance of light may be increased as the wavelength of the incident light into the ink structure 140 is increased.

Figure 22:
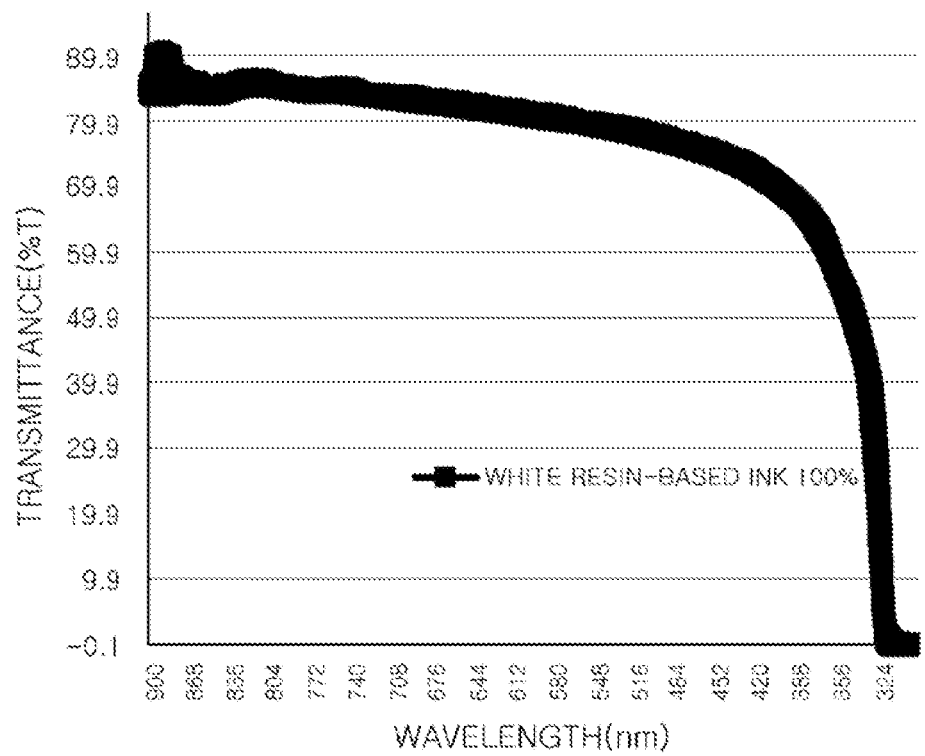
FIG. 22 is a graph showing a relation between the wavelength of incident light and the light transmittance of an ink structure.

FIG. 22 is a graph showing a relation between the wavelength of incident light and the light transmittance of an ink structure.

In FIG. 22, a horizontal axis of the graph refers to the wavelength of incident light and a vertical axis refers to the transmittance of the light. As described above, since the light transmittance of the ink structure 140 is increased as the composition ratio of the white resin-based ink is increased, in FIG. 22, a relation between a wavelength of light and the transmittance of the light is shown using an ink structure 140 formed of a 100% white resin-based ink as an example.

Referring to FIG. 22, it is determined that the transmittance of light is increased as the wavelength of the incident light is increased. More particularly, it is determined that the transmittance of light is sharply increased when a wavelength of the light is approximately equal to or less than 420 nm, and the transmittance of light is gradually increased when the wavelength of the light is approximately equal to or greater than 420 nm.

As described above, various exemplary embodiments of the optical analysis structures 100, 100a, 100b, 100c, and 100d are described. The optical analysis structures 100, 100a, 100b, 100c, and 100d may be applied to various fields in which optical analyses are needed. According to an exemplary embodiment, the optical analysis structures 100, 100a, 100b, 100c, and 100d may be applied when a sample is introduced and dried in the chamber 120 and delivered for optical analysis or may be applied to a platform structure of a microfluidic device. Hereinafter, it will be described that the case when the optical analysis structures 100, 100a, 100b, 100c, and 100d are applied to a platform structure of a microfluidic device.

Figure 23:
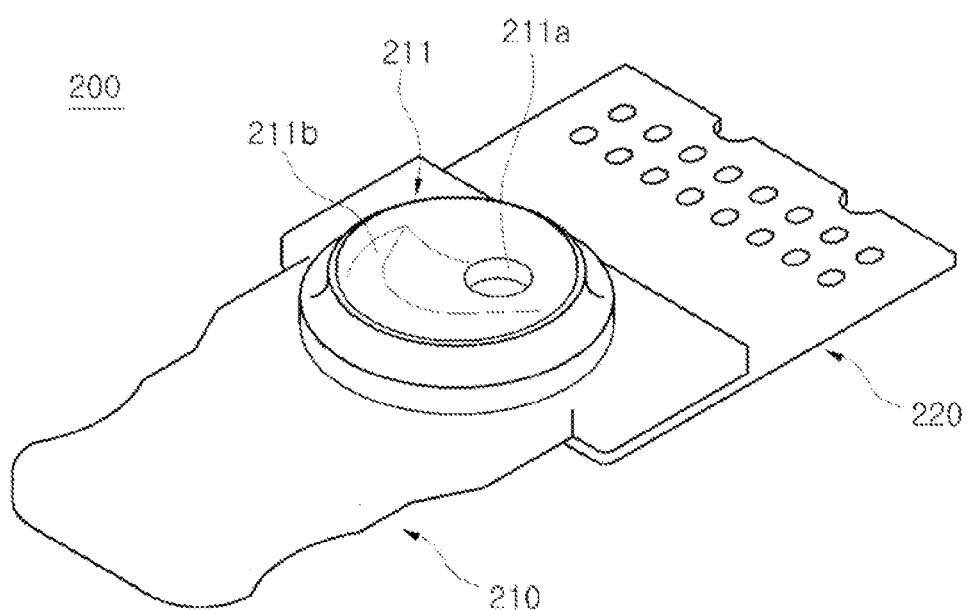
FIG. 23 is a view illustrating a microfluidic device, according to an exemplary embodiment.
Figure 24:
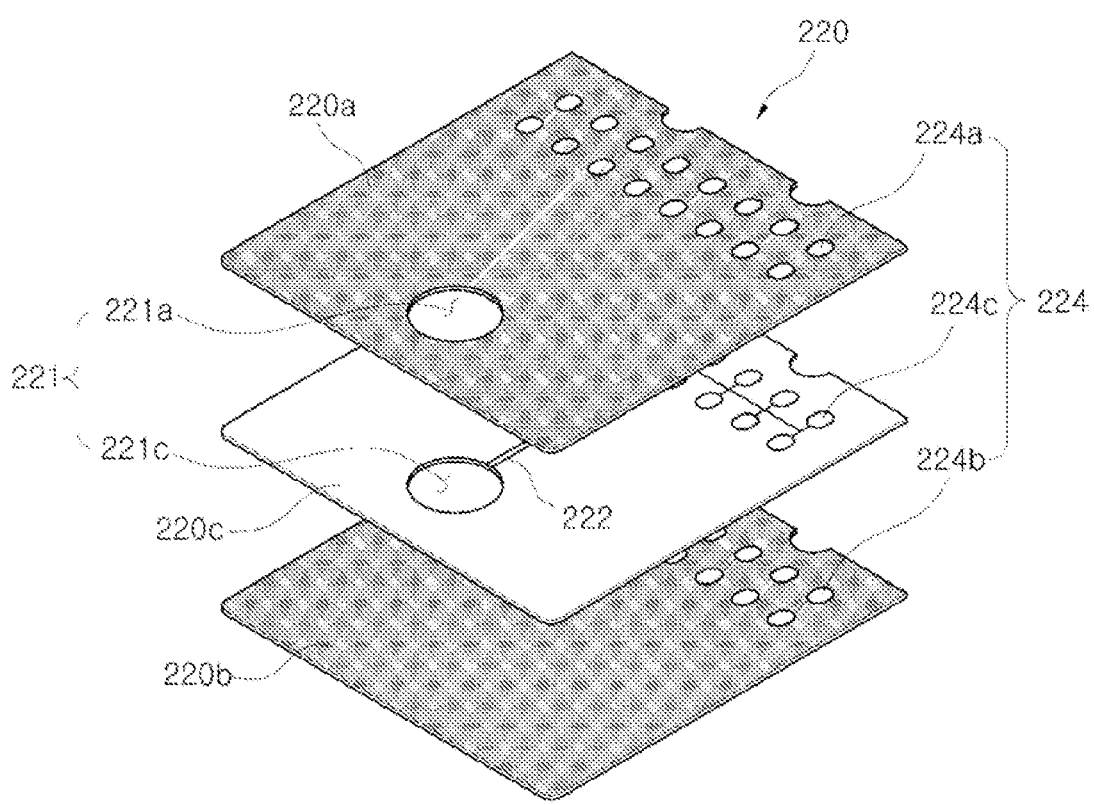
FIG. 24 is an exploded perspective view illustrating a structure of a platform configured to examine using the microfluidic device according to FIG. 23.

FIG. 23 is a view illustrating a microfluidic device 200 according to an exemplary embodiment, and FIG. 24 is an exploded perspective view illustrating the structure of a platform 220 configured to examine using the microfluidic device 200 illustrated in FIG. 23.

Referring to FIG. 23, a microfluidic device 200 according to an exemplary embodiment may include a housing 210, and a film-type platform 220 where optical analysis is performed.

The housing 210 supports the platform 220 and enables a user to simultaneously hold the microfluidic device 200. The housing 210 may be easily moldable and formed of a substance which is chemically and biologically inactive.

For example, any one of various materials, for example, an acryl such as polymethylmethacrylate (PMMA), a polysiloxane such as polydimethylsiloxane (PDMS), a polyethylene such as polycarbonate (PC), linear low density polyethylene (LLDPE), low density polyethylene (LDPE), medium density polyethylene (MDPE), and high density polyethylene (HDPE), plastic materials such as polyvinyl alcohol, very low density polyethylene (VLDPE), polypropylene (PP), acrylonitrile butadiene styrene (ABS), and a cyclic olefin copolymer (COC), glass, mica, silica, a semiconductor wafer, etc., may be used for the material of the housing 210.

The housing 210 may include a sample supplier 211 which is supplied with a sample. The sample to be supplied to the microfluidic device 200 may include a biological sample, such as, for example, any of blood, tissue fluid, lymphatic fluid, and urine. The sample supplier 211 may include a supply hole 211a in which a supplied sample flows into the platform 220 and an auxiliary supply 211b configured to assist the supply of the sample.

An user may drop a sample to be analyzed into the supply hole 211a by using a tool, such as, for example, a pipet or a spuit. In addition, the auxiliary supply 211b in which a slope is formed around the supply hole 211a in a direction of the supply hole 211a may guide a fluid sample which is dropped in a vicinity of the supply hole 211a to the supply hole 211a.

The platform 220 may be coupled to the housing 210 via a method in which the platform 220 may be fused to a bottom of the housing 210 of the sample supplier 211 or inserted into a certain groove formed in the housing 210.

Referring to FIG. 24, the platform 220 may be formed in a structure in which three plates are fused. The three plates may be divided into a top plate 220a, a bottom plate 220b, and an intermediate plate 220c, and the top plate 220a and the bottom plate 220b may be printed with ink and may protect a sample moving toward the chamber 120 from external light.

The top plate 220a and the bottom plate 220b of the platform 220 may be applied to the optical analysis structure 100 according to an exemplary embodiment. In particular, the optical analysis structure 100 may include a support 110 and an ink structure 140 coupled to the support 110 so as to form a chamber 120 on one surface of the support 110. According to an exemplary embodiment, a channel 130 may be formed in addition to the chamber 120, hereinafter, a case in which a plurality of the chambers 120 are formed by the ink structure 140 will be described as an exemplary embodiment.

The intermediate plate 220c of the platform 220 may formed with a porous sheet, such as, for example, cellulose. The porous sheet may be provided with a substance having a hydrophobic surface so as not to influence the moving of a sample, according to an exemplary embodiment.

The platform 220 may include a sample injection hole 221, a channel 222 where an injected sample moves, and chambers 224 where the optical analysis of a sample is performed.

When the platform 220 is formed in a triple layer structure, a top plate hole 221a configured to form a sample injection hole 221 may be formed in the top plate 220a, and chambers 224a may be formed on an area opposite the top plate hole 221a. At this time, a portion corresponding to each of the chambers 224a may be transparently formed. Meanwhile, in the bottom plate 220b, a part corresponding to each of the chambers 224b may also be transparently formed, and the reason why the part corresponding to the chambers 224b is transparently formed is to facilitate an examination of the optical characteristic of a sample accommodated in the chambers 224b.

According to an exemplary embodiment, a reagent may be accommodated inside the chambers 224b in advance. According to an exemplary embodiment, a reagent may be provided in a dried form to one surface of the chambers 224b. In this case, reaction between an injected sample and the reagent may occur, and an optical characteristic may be measured by a reaction occurring in the chambers 224b.

A intermediate plate hole 221c configured to form the sample injection hole may also be formed in the intermediate plate 220c, and when the top plate 220a, the intermediate plate 220c, and the bottom plate 220b are coupled, the top plate hole 221a and the intermediate plate hole 221c are overlapped and the sample injection hole 221 of the platform 220 may be formed.

Since the chambers 224c are formed in an area opposite the intermediate plate hole 221c, in an area of the intermediate plate 220c, the chambers 224 may be formed by removing areas corresponding to the chambers 224c from the area of the intermediate plate 220c to form circular shapes, rectangular shapes or the like, and coupling the top plate 220a, the intermediate plate 220c, and the bottom plate 220b to each other.

A channel 222, which is a path in which an injected sample moves, may be formed in the intermediate plate 220c. The channel 222 may have a width of about 1 μm to 500 μm, and a sample introduced through the sample injection hole 221 may move to chambers 224c due to the capillary force of the channel 222. The width of the channel 222 described above is only one exemplary embodiment which may be applied to a microfluidic device 200, and the exemplary embodiment is not limited to the value described above.

When a sample is supplied to the sample supplier 211 of the microfluidic device 200, the supplied sample flows into the platform 220 through the sample injection hole 221, and the introduced sample moves to the chamber 224 along the channel 222. When a reagent is stored in the chamber 224, the sample may react with the reagent. The sample accommodated in the chamber 224 may be provided for optical analysis, in this case, as illustrated in FIGS. 17, 18, 19, and 20, optical measurement data having uniform dispersion may be obtained.

As is apparent from the above description, the expected effects of the optical analysis structure in accordance with exemplary embodiments are as follows.

Various types of samples used for optical analysis can be easily transported by forming an ink structure using a resin-based ink and a pigment-based ink.

In addition, the uniformity of the optical analysis result can be secured by uniformly accommodating a sample in a chamber.

Although a few exemplary embodiments of an ink optical analysis structure are described above, the present inventive concept is not limited to the exemplary embodiments described above and should be understood to include variations within a range which may be easily conceivable to those of skill in the art.

What is claimed is:

1. A structure for optical analysis, comprising:
a support; and
an ink structure coupled to the support to form a chamber having a bottom surface and side surfaces,
wherein the ink structure comprises:
a first ink structural component configured to form a first sidewall of the ink structure and having a first slope with respect to a direction of a center of the chamber; and
a second ink structural component configured to form a second sidewall of the ink structure positioned under the first sidewall of the ink structure and having a second slope with respect to the direction of the center of the chamber,
wherein the first slope is different from the second slope,
wherein the ink structure is formed by coating an ink composition that includes a pigment-based ink and a resin-based ink,
wherein the second ink structural component has a higher lipophilicity than the first ink structural component, and
wherein the first sidewall and the second sidewall form one of the side surfaces of the chamber.

2. The structure of claim 1, wherein a slope of a longitudinal section of the second ink structural component decreases along a direction of the support.

3. The structure of claim 1, wherein a longitudinal section of the second ink structural component has a parabolic shape or a Gaussian distribution shape.

4. The structure of claim 1, wherein a diameter of the chamber decreases from a starting point of the second ink structural component in a direction of the support.

5. The structure of claim 1, wherein the ink structure forms a channel on one surface of the support.

6. The structure of claim 5, wherein a width of the channel decreases from a starting point of the second ink structural component in a direction of the support.

7. The structure of claim 1, wherein the first ink structural component is formed of the pigment-based ink and the resin-based ink.

8. The structure of claim 1, wherein the second ink structural component is formed of the resin-based ink.

9. The structure of claim 1, wherein the second ink structural component is formed by the resin-based ink in the ink composition flowing downward in a gravitational direction.

10. The structure of claim 1, wherein a weight of the pigment-based ink comprises between 30% and 70% of a total weight of the ink composition and a weight of the resin-based ink comprises between 30% and 70% of the total weight of the ink composition.

11. The structure of claim 1, wherein the ink composition further includes a curing agent and a retardant, and wherein a combined weight of the curing agent and the retardant comprises between 10% and 20% of a total weight of the ink composition.

12. The structure of claim 1, wherein a transmittance of the ink structure increases in correspondence with an increase of an ink composition ratio of a white resin-based ink included in the ink composition.

13. The structure of claim 1, wherein a transmittance of the ink structure increases in correspondence with an increase of a wavelength of light that is incident onto the ink structure.

14. The structure of claim 1, wherein the pigment-based ink includes at least one from among rutile, anatase, antimony oxide, zinc, calcium carbonate, silica, cadmium, chromium, cobalt, copper, iron oxide, lead, manganese, mercury, titanium, carbon, clay earth, ultramarine, alizarin, alizarin crimson, gamboge, cochineal red, rose madder, indigo, indian yellow, tyrian purple, quinacridone, magenta, phthalo green phthalo blue pigment red 170, and diarylide yellow.

15. The structure of claim 1, wherein the resin-based ink includes at least one from among silicone, cryptal, a semiconductor, benzoin, petroleum, styrene, aniline, an amino group, amino alkyd, vinyl acetate, alkyd, epoxy, urea, a casting resin, toluene, plastic, polyamide, polyurethane, and amber.

16. The structure of claim 1, wherein the support is provided in a thin film shape of a film type.

17. The structure of claim 1, wherein the support is provided in a curved surface shape.

18. The structure of claim 1, wherein, in the support, one surface coupled to the ink structure is hydrophilic-processed.

* * * * *